US005102396A

United States Patent [19]
Bommarito

[11] Patent Number: 5,102,396
[45] Date of Patent: Apr. 7, 1992

[54] JEJUNOCATH AND SURGICAL PAD

[76] Inventor: Alexander A. Bommarito, 12555 W. Freeland Rd., Freeland, Mich. 48623

[21] Appl. No.: 688,838

[22] Filed: Apr. 22, 1991

[51] Int. Cl.$^5$ .............................................. A61M 5/32
[52] U.S. Cl. ..................... 604/175; 604/174
[58] Field of Search ............ 604/175, 174, 164, 264, 604/272, 280

[56] References Cited

U.S. PATENT DOCUMENTS

| | | | |
|---|---|---|---|
| 3,927,672 | 12/1975 | Garcia | 604/278 X |
| 4,311,148 | 1/1982 | Courtney et al. | 604/175 |
| 4,534,760 | 8/1985 | Raible | 604/175 |
| 4,685,901 | 8/1987 | Parks | 604/178 X |
| 4,687,471 | 8/1987 | Twardowski et al. | 604/175 |
| 4,946,444 | 8/1990 | Heimke | 604/175 |

Primary Examiner—Gene Mancene
Assistant Examiner—Jeffrey A. Smith
Attorney, Agent, or Firm—Merlin B. Davey

[57] ABSTRACT

The present invention provides a Jejunocath comprising a novel removable surgical fixed pad adapted to be fastened to the bowel wall and to the anterior abdominal wall, thereby holding the catheter in place and preventing leaking from the bowel into the peritoneal cavity. The invention also provides a unique adapter that inhibits catheter blockage of undissolved medications and feeding formulas, provides for ease of removal of trapped undissolved matter in the adapter and for high adhesion in the connection between the adapter and catheter, thereby preventing leaks and unintended removal of a universal "Y" port from the catheter.

4 Claims, 1 Drawing Sheet

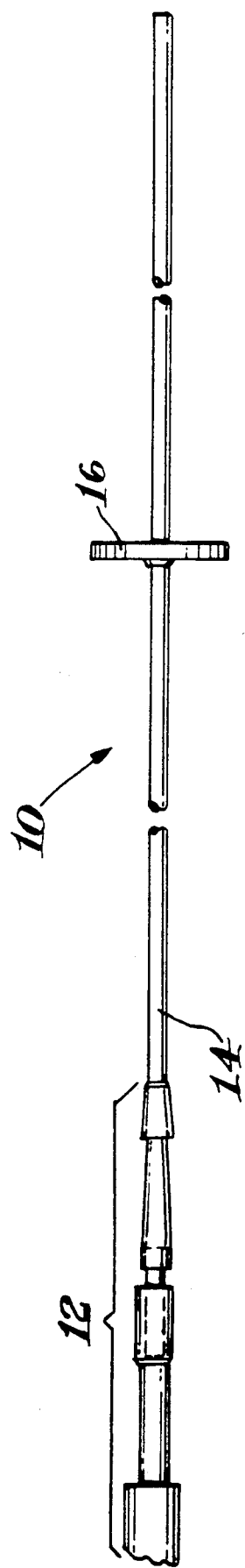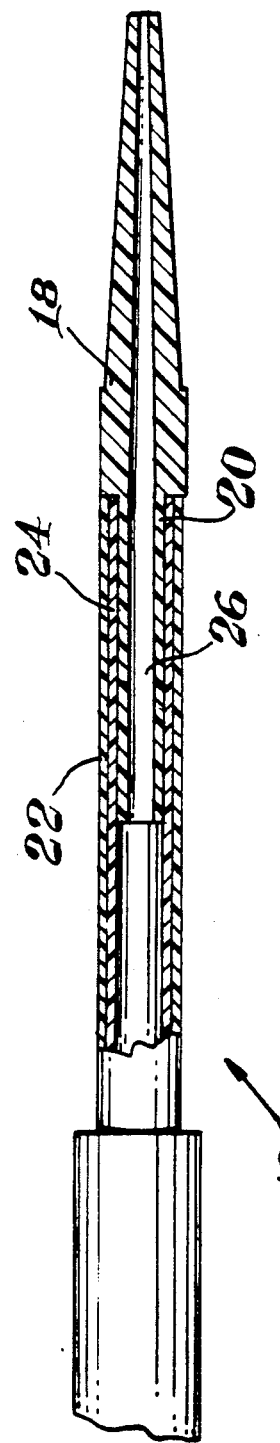

JEJUNOCATH AND SURGICAL PAD

BACKGROUND OF THE INVENTION

Intrajejunal feeding of liquid formula diets has been used in nutritional support for the past 50 years. Feeding delivered directly into the small intestine can take advantage of both the gastroesophageal and pyloric sphincters in preventing regurgitation. This technique is attractive because it may be used for both temporary and long-term feeding whenever small bowel motility and absorptive capacity are adequate. It may be used in spite of disease states and conditions which may alter gastric, biliary, and/or pancreatic function.

Intrajejunal feeding is indicated in cases of carcinoma of the esophagus, carcinoma of the stomach, radiation esophagitis, head and neck carcinomas, mechanical and motility disorder/dysphagia, esophageal stricture, gastric motility disorders, neuromuscular disorders and post surgical feeding.

Jejunostomy techniques of historical and practical interest include, for example, the techniques of Surmay, Maydl, Stamm and Witzel. Surmay's technique was a failure because of leakage of jejunal contents. The Witzel and Stamm jejunostomies are still in use, but are fraught with problems of leakage around the jejunostomy tube into the peritoneal cavity or onto the skin, bowel obstruction from the tube or from internal hernia, and the persistence of enterocutaneous fistula after the large tube is removed. The Maydl jejunostomy avoides these problems by use of the roux-en-y and affords permanence. It is more complicated and technically demanding. The use of the Maydl jejunostomy was more frequent in the early 1950s. The needle catheter jejunostomy (NCJ) is a modification of the Witzel jejunostomy evolved from the concept of using a fine catheter for intrajejunal feeding and from the availability of a variety of relatively low viscosity, complete liquid formula diets. The major problems with the (NCJ) are blocked, kinked and pulled catheters. The problems with jejunostomy techniques and equipment have limited the use of this technique. Current studies in nutritional support keep providing evidence of benefits of feeding this area of the bowel.

Standard feeding systems provide high rates of feeding in the range of 800 to 1200 ml. per hour. These rates are adjusted with a clamp or pump in normal patient feeding. In jejunal feeding high rates are not desirable and the standard feeding equipment is not advantageously employed.

SUMMARY OF THE INVENTION

The present invention comprises a Jejunocath comprising a medical grade silicon catheter and a novel removable surgical fixed pad adapted to be fastened to the bowel wall and to the anterior abdominal wall, thereby holding the catheter in place and preventing leaking from the bowel into the peritoneal cavity. The surgical fixed pad or "football" further inhibits the pulling out of the tube by the patient. The Jejunocath further comprises an adapter which provides for the connection of an 8 French (Fr.), i.e., having a diameter of about 100 thousandths of an inch catheter to a universal feeding port. The adapter has a 3-6 Fr., preferably about 4 Fr., inside diameter to stop occlusion of the 8 Fr. feeding tube. A French unit is approximatley 0.013" as can be seen from Parks U.S. Pat. No. 4,685,901, Col. 3, lines 47 to 50. The adapter of this invention advantageously reduces the fluid flow in the catheter by about 75%, i.e., to maximum rates of from about 200 to 300 ml. per hour.

DETAILED DESCRIPTION OF THE INVENTION

The invention is further illustrated by the accompanying drawings wherein:

FIG. 1 is a schematic drawing of the Jejunocath of this invention, and

FIG. 2 is a partially sectioned view of the adapter for the Jejunocath of this invention.

Referring to the drawings the Jejunocath (10) of this invention is seen to include adapter (12), catheter (14) and surgical fixed pad (16). Catheter (14) is advantageously made of medical grade silicon such as, for example, Silicon RX 65. The adhesive force of attachment between adapter (12) and catheter (14) is preferably at least 10 lbs., that is, a force of at least 10 lbs. is required to remove catheter (14) from adapter (12). Catheter (14) is advantageously size 8 Fr. O.D. Surgical fixed pad (16) is also preferably made of medical grade silicon, such as, for example, Silicon Q7-4840. Surgical fixed pad (16) is advantageously made in the shape of a football and has flexible edges adapted for suturing to the wall of the bowel and also to the anterior abdominal wall. The flexibility also insures ease of removal when enteral feeding is no longer necessary.

In FIG. 2, adapter (12) is shown in a partially sectioned view and is seen to have a tapered end (18) and a linear portion (20), said linear portion (20) being fitted within a concentric tube (22) and being attached thereto by a silicon adhesive (24). Tapered end (18) and linear portion (20) of adapter (12) are advantageously prepared of a generally rigid polyethylene. Passageway (26) in linear portion (20) advantageously has an inside diameter of about 7 Fr. and in tapered portion (18), the inside diameter is decreased generally uniformly to an outlet of from about 3-6 Fr., preferably about 4 Fr. Tube (22) is advantageously prepared of polyvinyl chloride and is generally rigid with an inner 8 Fr. Silicon RX 65 tube fixed inside.

In placing the Jejunocath of this invention, the patient is placed in the supine position and the abdomen is prepared and draped in the usual sterile manner. A 5 cm. transverse left upper abdominal incision is made and dissection carried through the subcutaneous tissues in the transverse plane down to the rectus fascia. The rectus fascia is opened in the transverse direction and the rectus muscle is either divided or split longitudinally and retracted medially and laterally revealing the transversus fascia and peritoneum below. These layers are elevated between hemostats and divided and the peritoneal cavity is entered. The peritoneum is opened in the transverse plane throughout the length of the wound. A self-retaining retractor may be placed to provide exposure. The jejunum is localized and traced back to the ligament of Treitz. A segment of jejunum approximately 6 to 10 inches distal to the ligament of Treitz is selected for the tube insertion site.

When the proximal jejunal site has been selected and verified, approximately 10 cc. of sterile saline are injected subserosally in order to produce edema and increase the thickness of the bowel wall for a length of approximately 3 cm. A purse string suture of 3-0 silk is then placed at the proximal margin of the subserosal injection. A needle is placed through the center of the purse-string suture into the subserosal plane and guided through the injected area and finally punched through the mucosa into the lumen of the bowel. A guidewire is placed through the needle and the needle is removed.

The dilator and sheath are then passed over the guidewire creating a subserosal tunnel leading into the lumen of the bowel. The guidewire and tunneler are then removed and the Jejunocath is placed through the sheath and into the lumen of the bowel. The sheath is then split and removed and the entire length of the Jejunocath is placed into the bowel such that the "football" lies against the bowel wall.

Attention is then turned to the anterior abdominal wall and a suitable exit site, just above or below the incision is selected for the catheter. The catheter is connected to the barbed end of the trocar and inserted through the peritoneum at the preselected site. The proximal end of the Jejunocath is pulled through this tunnel to exit through the abdominal wall. A skin disc as is known in the art is then slid own the catheter towards the skin. The Prolene suture on the straight needle is then utilized to fix the catheter and bowel in place. The suture is placed with the straight needle through the skin disc and into the abdominal wall next to and parallel to the catheter exit track emerging on the peritoneal side next to the catheter. This same stitch is then placed through the "football" edge, and continued as a seromuscular suture placed across the bowel towards the opposite football edge, then placed through this edge of the "football" and back through the entire thickness of the anterior abdominal and back through the skin disc on the opposite side of the catheter. A second similar suture is placed such that the seromuscular portion of the suture is in the bowel or the side of the tube opposite to the first suture. These sutures are then pulled up such that the bowel is firmly opposed to the bowel wall, the sutures are tied over the skin disc. It is unnecessary to tie the external portion of the catheter in place.

The end of the catheter is then snipped off to remove the trocar. The Y-port is then inserted into the end and 10 cc. of saline are injected through the catheter to verify its position and the free flow of saline into the lumen of the bowel. The tube is then capped. The wound is then closed in layers with 2-0 absorbable suture in the peritoneum and transversus abdomenus layers, 0 prolene suture in the rectus sheath, and the skin is closed with a running subcuticular suture of 4-0 Prolene.

The clinical trials with the jejunocath have demonstrated three major advantages. First, the "football" or surgical fixed pad stops the leaking of jejunal contents. This stops major infectious problems in the peritoneal cavity and the skin. Yet when the feeding is no longer needed the jejunocath can be pulled out and the "football" or surgical fixed pad will deform and pull out the exit track. In addition the "football" or surgical fixed pad stops the tube from being pulled out by the patient.

The eight French size and hardness of the tube is its second advantage. The patient can be fed all types of feeding formulas without inhibiting flow or blocking the feeding tube. Surgical techniques will not cause kinking of the tube with placement as is seen with the (NCJ). The last and major advantage is a small, preferably about 7 Fr. start and about 4 Fr. end, 3.5 centimeters in length plastic adapter with high adhesive force.

Its major function is to connect tenaciously the 8 Fr. catheter to the universal "Y" feeding port, but it also functions to stop the blockage of the surgically placed jejunostomy feeding tube. This is accomplished with the size and change in size over a short distance, i.e., a Venturi effect is created thereby increasing the emulsion stability coming out of the 4 Fr. end of the feeding port into the 8 Fr. catheter and inhibiting blockage. Under pressure feeding formulas will be re-emulsified. Small hard rock-like insolubles will not pass the 4 Fr. tube and can be washed out with ease, by removal of the adapter from the feeding tube. The last advantage with the small adapter is to slow the rate of feeding into the small intestine. If enteral feedings are administered too fast a dumping syndrome can result. The rate of feeding will vary with the viscosity of the liquid formula diet and the head pressure or height of the feeding bag. Maximum rates are of the normal rate seen with common feeding formulas with a range of 15-25% and rates can be set at a safe level by control of the head pressure (adjusting of the feeding bag height) on set up. This eliminates the potential problem of feeding too fast and need for a feeding pump.

Various modifications may be made in the present invention without departing from the spirit or scope thereof as will be understood by those skilled in the art.

I claim:

1. A needle catheter Jejunocath consisting essentially of a medical grade silicon catheter and a single removable surgical fixed pad attached to said catheter and wherein said surgical pad is adapted to be fastened to a bowel wall and an anterior abdominal wall.

2. Jejunocath of claim 1 further comprising an adapter having a central passageway generally uniformly tapering from 7 Fr. to 3-6 Fr. whereby the said adapter inhibits blockage when medications and feeding formulas are infused thererin.

3. Jejunocath of claim 2 wherein said adapter has a rate limiting capacity of fluid flow of at least 75% of standard feeding rates of 800 to 1,200 ml. per hour.

4. Jejunocath of claim 1 wherein said adapter has an adhesive force of at least 10 lbs. with said medical grade silicon catheter.

* * * * *